United States Patent [19]

Popp

[11] Patent Number: 5,421,344
[45] Date of Patent: Jun. 6, 1995

[54] METHOD AND MEANS OF DETERMINING THE HEALTH CONDITION OF A LIVING CREATURE

[75] Inventor: Fritz-Albert Popp, Kaiserslautern, Germany

[73] Assignee: Max Reinhard, Bad Homburg, Germany

[21] Appl. No.: 78,324
[22] PCT Filed: Oct. 15, 1992
[86] PCT No.: PCT/EP92/02380
  § 371 Date: Jun. 23, 1993
  § 102(e) Date: Jun. 23, 1993
[87] PCT Pub. No.: WO93/07809
  PCT Pub. Date: Apr. 29, 1993

[30] Foreign Application Priority Data

Oct. 23, 1991 [DE] Germany .................. 41 34 960.1

[51] Int. Cl.⁶ .............................................. A61B 5/05
[52] U.S. Cl. .................................................. 128/734
[58] Field of Search .................. 128/734, 731–732, 128/665, 664, 630

[56] References Cited

U.S. PATENT DOCUMENTS

| | | | |
|---|---|---|---|
| 3,450,866 | 6/1969 | Jaccard ..................... | 235234/61.11 |
| 3,939,841 | 2/1976 | Dohring et al. .............. | 128/303.19 |
| 4,310,003 | 1/1982 | Schlager ..................... | 128/736 |
| 4,502,487 | 3/1985 | Dubrucq et al. ............... | 128/665 |
| 4,683,892 | 8/1987 | Johansson et al. ............. | 128/731 X |
| 4,802,488 | 2/1989 | Eckerle ....................... | 128/672 |
| 4,846,190 | 7/1989 | John .......................... | 128/731 |
| 4,852,579 | 8/1989 | Gilstad et al. ................ | 128/665 |
| 4,947,862 | 8/1990 | Kelly ......................... | 128/734 |
| 4,960,109 | 10/1990 | Lele .......................... | 607/97 X |
| 5,203,344 | 4/1993 | Scheltinga et al. ............. | 128/734 |
| 5,272,624 | 12/1993 | Gisser et al. ................. | 128/734 X |

FOREIGN PATENT DOCUMENTS 2236514 2/1975 France .
2418646 9/1979 France .

OTHER PUBLICATIONS

Journal "Erfahrungsheilkunde" pp. 240–247 vol. 4/1990.

Primary Examiner—Angela D. Sykes
Attorney, Agent, or Firm—Griffin, Butler Whisenhunt & Kurtossy

[57] ABSTRACT

A method of determining the health condition of a living creature comprises the steps of detecting a selected physiological characteristic, e.g. the conductivity of the skin, of the living creature at a statistically significant plurality of measuring points distributed over a defined body portion of the living creature, determining, e.g. by means of a computer, the statistical distribution of the measured values and comparing the statistical distribution of the measured values to a reference statistical distribution of the selected physiological characteristic. The said reference statistical distribution is a logarithmic distribution which is determined according to the calculating methods of statistics by means of the computer directly from the measured values obtained for the individual tested living creature. The invention for the first time permits a reliable indication as to overall health condition of a human or animal.

12 Claims, 4 Drawing Sheets

BRONCHIAL ASTHMA (BEFORE TREATMENT)

BRONCHIAL ASTHMA (AFTER TREATMENT)

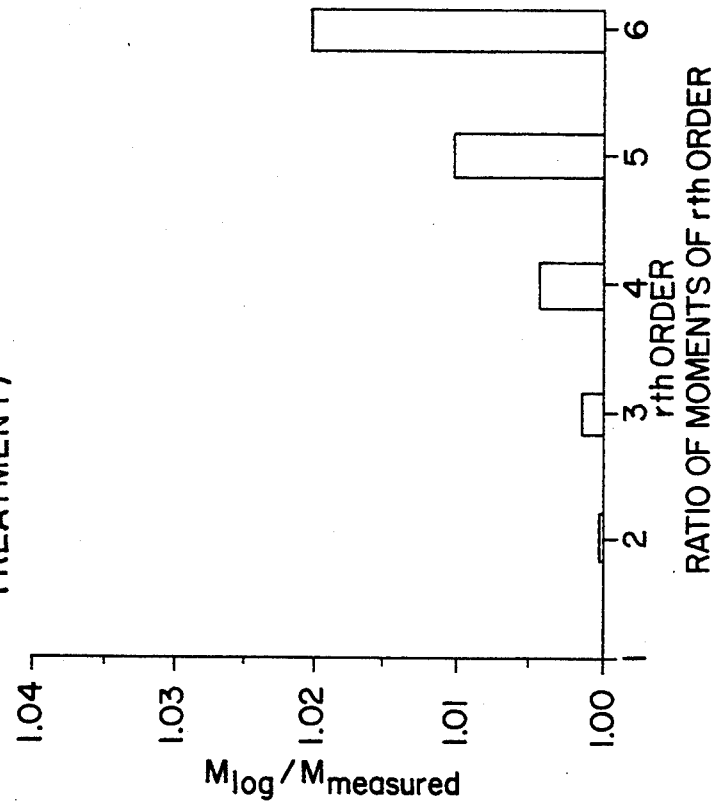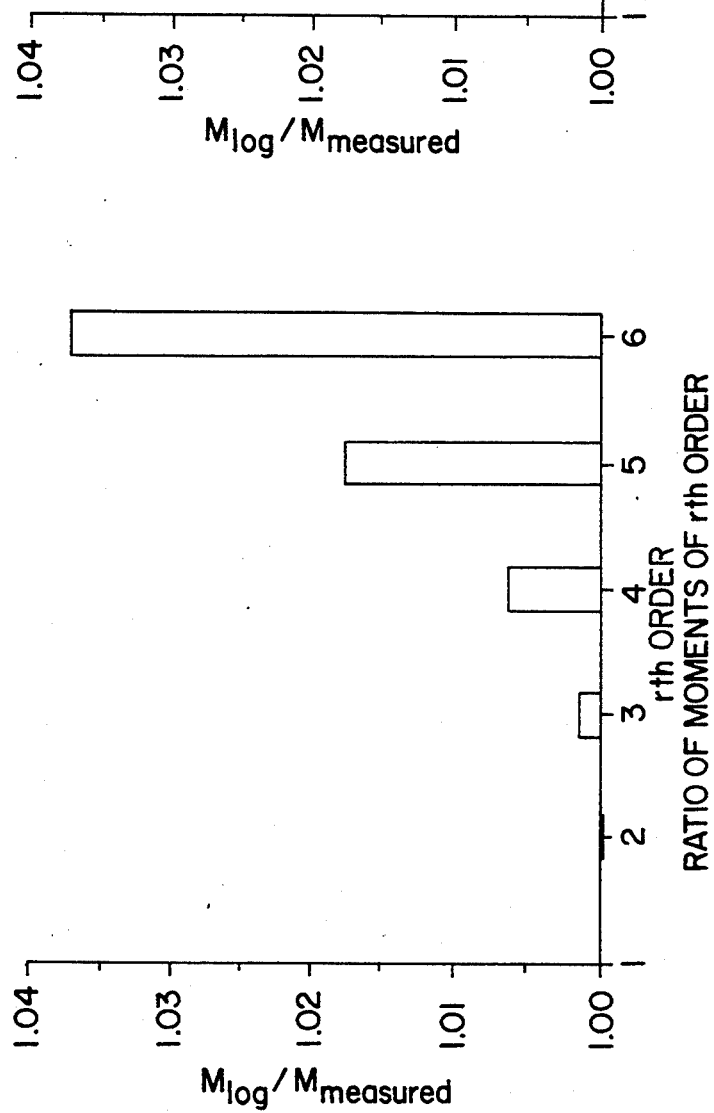

METHOD AND MEANS OF DETERMINING THE HEALTH CONDITION OF A LIVING CREATURE

The invention relates to a method and a means of determining the health condition of a living creature on the basis of a comparison of a selected measured physiological characteristic of the living creature to a corresponding reference characteristic of the healthy condition.

The invention relates in particular to a method and a means of making possible an indication as to the overall health condition of a human or animal.

All instruments employed in medical diagnosis acquire a specific characteristic or specific parameter of a patient, e.g. pulse frequency, blood pressure, chemical composition of the blood etc. Since the normal ranges are known from the corresponding measured values of a healthy population, a criterion for the nature and severity of an illness can be established from the deviation of the actual values from the standard. The diagnosis is made from a plurality of different characteristics, medical experience being the determining factor in selecting the characteristics in each case. However, until now it has not been achieved to establish explicit and objective criteria for the "overall health" condition of a patient even by means of "alternative" methods.

Accordingly it is an object of the present invention to provide a method and means of the aforementioned kind which permit a reliable indication as to the overall health condition of a test person. In addition, the invention is intended to permit establishing to what degree the condition of the test person deviates overall from an ideal condition. The means are also intended to permit economic examination of a large number of test persons by enabling the examination to be made quickly and cost effectively.

The method according to the invention is characterized by the steps of detecting the selected physiological characteristic at a statistically significant plurality of measuring points distributed over a defined body region of the living creature, determining the statistical distribution of the measured values obtained for the said body region, and comparing the statistical distribution of the measured values to a reference statistical distribution in the form of the logarithmic normal distribution of the selected physiological characteristic. It is particularly advantageous and thus preferred to determine the said logarithmic distribution from the measured values obtained for the tested person. Due to it being easily available the skin of the test person is preferably used as the body region in question, the electrical conductivity of the skin or its radiation intensity being taken as the physiological characteristic. However, the invention is restricted neither to such special physiological characteristics nor to the body region "skin". Instead, the method according to the invention is generally applicable also to other characteristics and other suitable internal or external body regions.

The invention makes use of the fact that according to the rules of statistics, parameters irrespective of, which kind always follow a specific statistical distribution (viz. L. Sachs: Statische Auswertungsmethoden, 2nd Edition, Springer Verlag Berlin 1969, pages 105–106), "statistical distribution" being understood to mean the probability function $p(x)$ indicating the probability or frequency of encountering a specific measured value x in an arbitrary test object, whereby x can encompass the total scale of values available.

The physiological characteristics of living creatures such as, for instance, body height, blood pressure, drug tolerance etc. are also always distributed according to a logarithmic normal distribution, the reason for this being assumed a multiplicative configurational principle (viz. e,g, also: H. Gebelein and H. J. Heite, Klin. Wschr. 28 (1959), page 41). Within the framework of tests according to the invention it was further established that the logarithmic normal distribution exists not only for a specific characteristic in measurements made on a plurality of individuals, but also for a single healthy individual when the characteristic concerned is measured on a sufficiently large number of measured values of the individual. "Sufficiently" in this context means no further significant change occurring in the resulting statistical distribution when the number of measured values is further increased.

The ideal log-normal distribution of such measured values obtainable from a single test person exists only when the ideal "multiplicative configuration principle"—i.e. the combined effect of all sub-units in space and time in the sense of an ideal organization—is satisfied. Therefore, by comparing the statistical distribution, as measured or as determined by suitably transforming the measured values, to the logarithmic normal distribution an explicit classification of the "overall" condition with reference to the condition of an ideal biological organisation can be obtained. Further indications in this respect can be obtained in addition to the comparison when according to further embodiments of the invention the deviations of the same order, e.g. the relative differences of the moments of the first to nth order are determined and/or the change in the statistical distribution with time is established and subjected to a correlation analysis. The temporal development of the statistical distribution describes the dynamic behaviour of the network of internal dependencies forming the basis of the measurement. The correlation analysis (e.g. factor analysis) enables the internal relationships between the skin areas to be described dynamically for a known assignment of the measured values, these relationships including all interrelationships with the organs.

From this it follows that in the sense of the invention a test person is able to be classified "overall" as being "healthy" when his distribution function $p(x)$ does not significantly deviate from $p_n(x)$, where $p(x)$ represents the measured distribution function and $p_n(x)$ the ideal distribution function for a healthy individual. This distribution function $p_n(x)$ is a logarithmic normal distribution and can be established according to the invention from the measured values of the test person, i.e. it not being necessary to obtain the normal distribution as an empirical function of the measured values of a plurality of healthy test persons.

Inversely the "illness condition" in this "overall" sense can be defined by the systematic (and fully) listed deviations between the functions $p(x)$ and $p_n(x)$. One salient advantage of the method according to the invention is, among other things, that there is no need to recourse to establishing the measured values of a plurality of test persons, but to calculate the ideal distribution function applicable to the individual test person directly from the measured values and to compare it to the actual statistical distribution.

In accordance with a further aspect of the invention a means of implementing the method according to the invention is provided which includes a sensor arrangement for detecting a selected physiological characteristic of the living creature at a plurality of measurement points distributed over a body region and outputting corresponding signals, means for processing the signals output by the sensor arrangement, and means for calculating from the signals output by said signal processing means the actual statistical distribution and the logarithmic normal distribution of the signal-related measured values of the physiological characteristic obtained. Obtaining the measured values is particularly uncomplicated and speedy when according to a further embodiment of the invention the sensor arrangement includes a plurality of contact or proximity sensor elements distributed over a defined surface area as well as a means of successively scanning them. As regards further embodiments of the invention reference is made to the claims.

BRIEF DESCRIPTION OF THE DRAWINGS

The invention will now be explained in more detail with reference to an example and the drawing in which.

FIGS. 2a, 2b shows the ratio of the moments of the rth order (r=1...6) for a logarithmic normal distribution and a measured distribution before treatment (FIG. 2a) and after treatment (FIG. 2b).

DETAILED DESCRIPTION OF THE DRAWINGS

Figure 3:
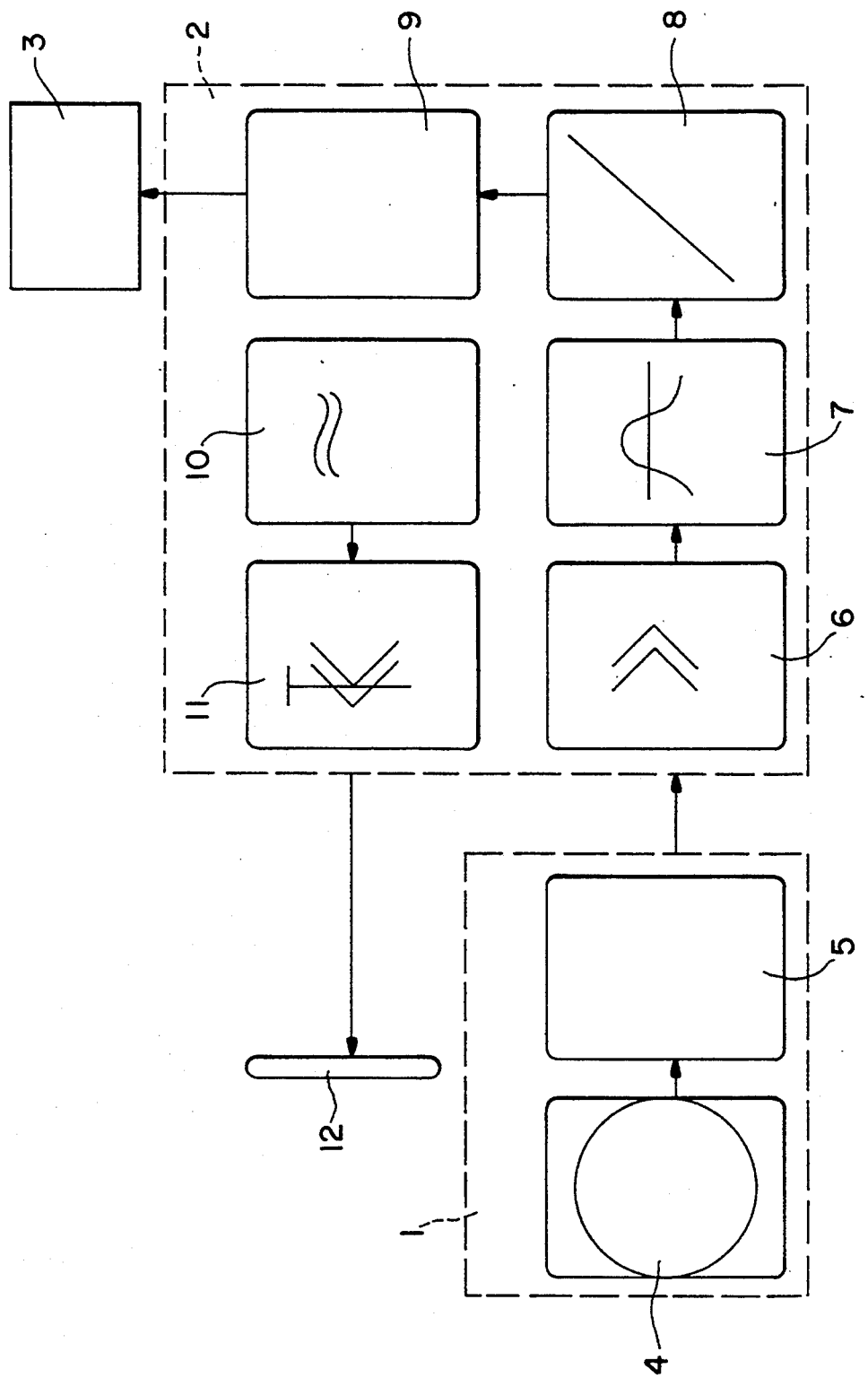
FIG. 3 is a block diagram of a means of obtaining the conductivity of the skin and for processing the obtained measured values according to one embodiment of the invention
Figure 4:
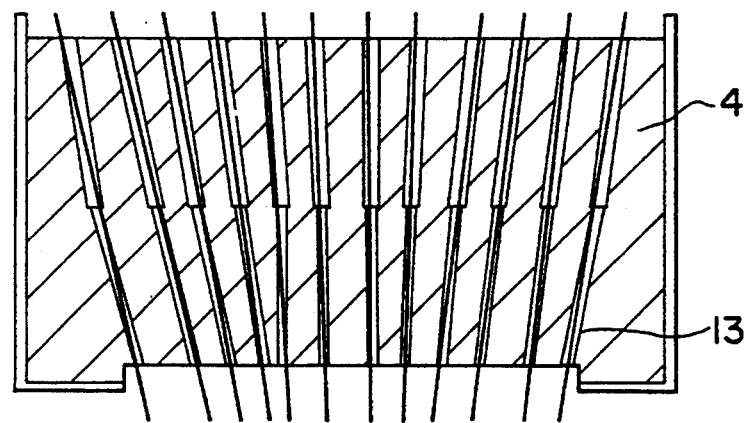
FIG. 4 is a section view showing the sensor member of a sensor arrangement of the means according to FIG. 3
Figure 5:
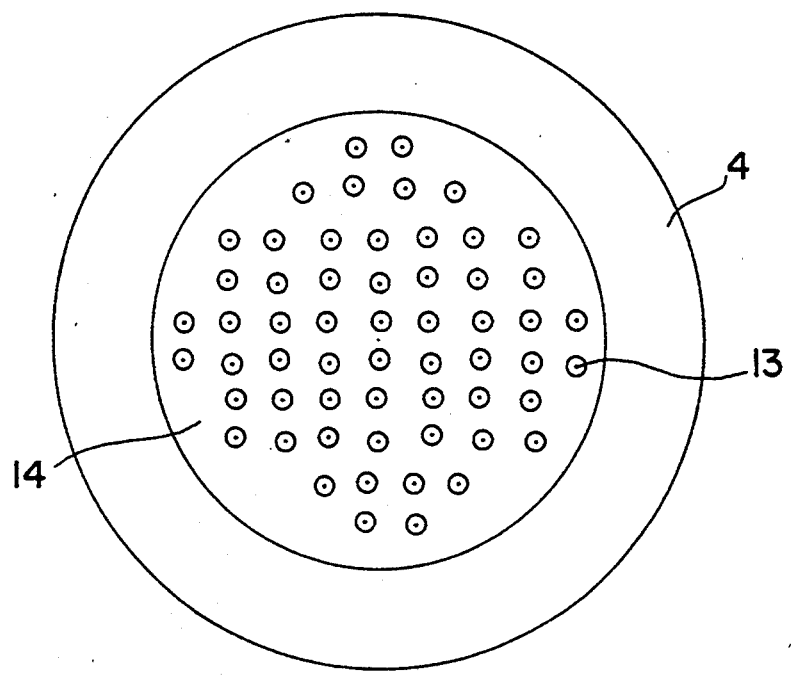
FIG. 5 is a view of the sensor arrangement according to FIG. 3 as seen from below.

With reference first to FIGS. 3-5 one embodiment of a means or an apparatus for implementing the method according to the invention will now be described on the basis of measuring the electrical conductivity of the skin of a patient. The means includes according to FIG. 3 a sensor arrangement 1, a signal processing means 2 and a processor 3.

The sensor arrangement 1 can be a multichannel electrode comprising a sensor member 4 and a scanner member 5. The sensor member 4 is shown in more detail in FIGS. 4 and 5 and includes a plurality of needle-shaped electrodes or sensor elements 13 located longitudinally shiftable in a base member. Each sensor element 13 is assigned a spring to preload the sensor element in its initial position as shown in FIG. 4 in which the free ends of the sensor elements 13 protruding from the base member are located in a plane which may be flat or curved in accordance with the curvature of a bodily region, e.g. of the hand to be tested of a test person. The preloading of the sensor elements 13 causes them to exert a defined pressure on the skin surface when brought into contact therewith. An "adequate" number of sensor elements 13 is provided, it having been established that a number between 50 and 150, e.g. 60 sensor elements 13 is adequate in the aforementioned sense.

The sensor elements 13 are further distributed over a defined e.g. circular measurement area 14 of the sensor member 4. The scanner member 5 of the sensor arrangement 1 which can be of a type as generally known to the person skilled in the art, serves to successively scan the individual sensor elements 13 and to furnish the signals characterizing the conductivity values obtained at the individual sensor elements 13 to the processing means 2. The measurement values obtained may be e.g. "pointer drops" of "electroacupuncture" methods as usual nowadays which result as soon as the measurement electrode is applied to the measurement point with constant contact pressure on the basis of a maximum value.

The signal processing means 2 includes an amplifier 6 for amplifying the individual signals output by the sensor arrangement 1. The output of the amplifier 6 is connected to a bypass filter 7 which has the effect of filtering out any noise signals from the measurement signals. The filtered measurement signals are then applied to an AD converter 8. The digital output signals of the AD converter 8 are passed via an interface 9 of the signal processing means 2 to a processor 3. In this way the processor 3 receives digital signals which are amplified and free of noise, these signals corresponding to the measurement signals established by the sensor arrangement 1.

In addition, the signal processing means 2 includes a means of applying a defined reference AC voltage to a suitable body location of the test person. If the measured values are obtained on one side of the hand of the test person, a suitable measurement point for applying the reference voltage is the other side of the hand. The means for applying the reference voltage includes a voltage generator 10, the output of which is furnished to a suitable hand electrode 12 via a variable amplifier 11.

The processor 3 establishes from the signals output by the processor 2 the logarithmic normal distribution $p_n(x)$ corresponding to the measurement values obtained from and initially applicable to the test person, i.e. the ideal distribution function of the latter and, furthermore, the real distribution function $p(x)$. The logarithmix normal distribution is that which has the same mean value $\bar{x}$ and the same dispersion $\sigma$ as the measured distribution $p(x)$. From the deviations between $p(x)$ and $p_n(x)$ an indication is possible as to the nature and scope of the health problems involved.

The processor 3 also establishes other parameters characteristic of the health condition of the test person such as e.g. the ratio of the moments of the rth order of the logarithmic normal distribution to the measured statistical distribution. The result of the computations can be displayed on a computer monitor and/or printed out in the form of graphs or tabulated data. The processor 3 also handles localization and computation of the maximum conductivity value within the measured matrix.

Computation of the measured distribution function $p(x)$ and the logarithmic normal distribution $p_n(x)$ is explained in the following on the basis of an example computation in which the numerical values are those as tabulated in Table 1.

Example computation

Figure 1A:
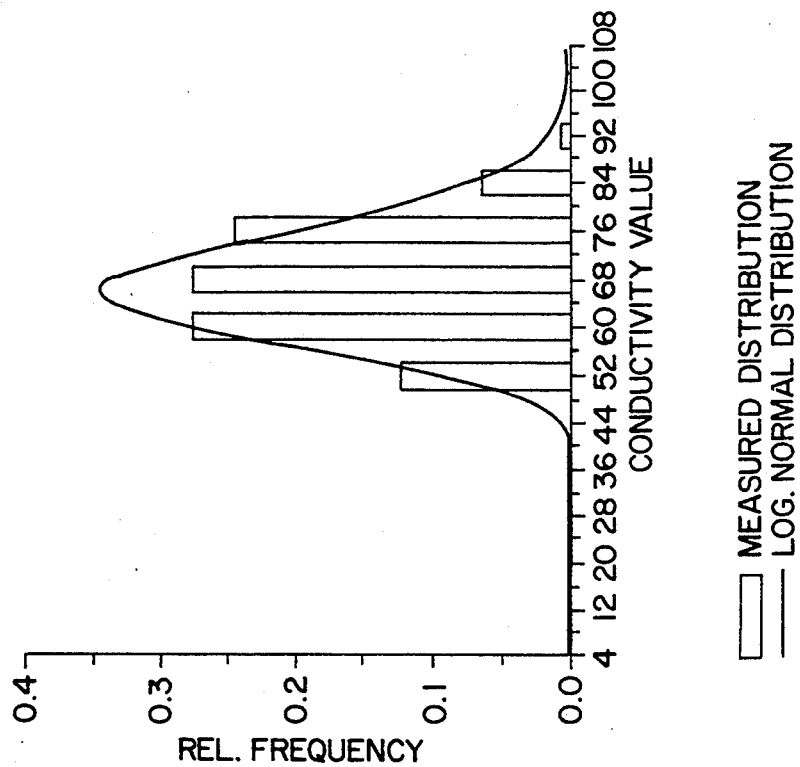
FIGS. 1a, 1b shows the statistical distribution of the conductivity values of the skin of a patient before treatment (FIG. 1a) and after treatment (FIG. 1b) as compared to the logarithmic normal distribution employing the same mean values and variances in each case.

1. Dividing the frequency values into n classes, whereby in this case n=14. The class mean values are given over the full measurement range (as stated in Tab. 1) as 4, 12, 20, 28, ..., 108 in steps of 8 (as the x axis of FIG. 1a, b shows). In the following these values are identified $k_m(i)$ where $i=1, \ldots, 14$. For example $k_m(2)=12$, $k_m(3)=20$.

2. Computation of the measured distribution p(x)

a) Computation of the sum of the frequency values (p(x)) given in Table 1. As an example the values before treatment are given.

The sum stated N in the following is $$N = \sum_{i=1}^{k=14} P(x_i)$$

Thus $N=0+14+22+34+18+32+2+0=122$

The frequency values P(x) are then divided by the sum N $$\frac{0}{122} = 0, \frac{14}{122} = 0.115, \frac{22}{122} = 0.18, \frac{34}{122} = 0.279,$$

$$\frac{18}{122} = 0.148, \frac{32}{122} = 0.262, \frac{2}{122} = 0.016, \frac{0}{122} = 0.$$

Expressed as an equation:

$$p(x_i) = \frac{1}{N} P(x_i) = P_i$$

This measured distribution is depicted as a bar graph.

3. Computation of log normal distribution

Computing central value $\bar{x}$ and dispersion $\sigma$:

$$\bar{x} = \frac{1}{N} \sum_{i=1}^{k} P(x_i) * Km(i)$$

$$\sigma = \sqrt{\frac{1}{N-1} \sum_{i=1}^{k} (Km(i) - \bar{x})^2 P(x_i)}$$

EXAMPLE $$\bar{x} = \frac{1}{122} (14 * 52 + 22 * 60 + 34 * 68 +$$

$$18 * 76 + 32 * 84 + 2 * 92) = 70.49.$$

$$h\sigma = (52 - 70.49)^2 * 14 + (60 - 70.49)^2 * 22 +$$

$$(68 - 70.49)^2 * 34 + (76 - 70.49)^2 * 18 +$$

$$(84 - 70.49)^2 * 32 + (92 - 70.49)^2 * 2$$

$$\sigma = \sqrt{\frac{1}{121} * h\sigma}$$

expedients:

$$\kappa = \sqrt{\ln\left(\frac{\sigma^2}{\bar{x}^2} + 1\right)} = 0.156.$$

$$\mu = \ln \bar{x} - \frac{\ln \sigma^2}{2} = 4.243$$

log. normal distribution $$p_n(x_i) = \frac{1}{\sqrt{2\pi} \ln \sigma \, Km(i)} \exp\left(-\frac{1}{2}\left(\frac{\ln Km(i) - \mu}{\kappa}\right)^2\right)$$

Example for class value 68:

$$p_n(68) = \frac{1}{\sqrt{2 * \pi} * 0.156 * 68} \exp\left(-\frac{1}{2}\left(\frac{4.219 - 4.243}{0.156}\right)^2\right) = 0.121$$

All values of $p_n(x_i)$ are then summed over all i's and divided by the total sum. This total sum $$\sum_{i=1}^{k=14} p_n(x_i) = 0.412$$

so that e.g. at the mark 68 is not 0.121 but according to this standarization $$p_n(68) = \frac{0.121}{0.413} = 0.294$$

EXAMPLE

On a patient seriously afflicted with bronchial asthma the electrical conductivity values were established at 112 measurement points on the skin and the relative frequency of the values entered on a scale from 0 to 100.

The frequencies at which the values in the various scale ranges were measured are listed in Table 1 for $n=8$ measurement intervals. The left-hand column relates to the values prior to treatment, those in the right to the values following relatively successful treatment (patient suffered less).

Figure 1B:
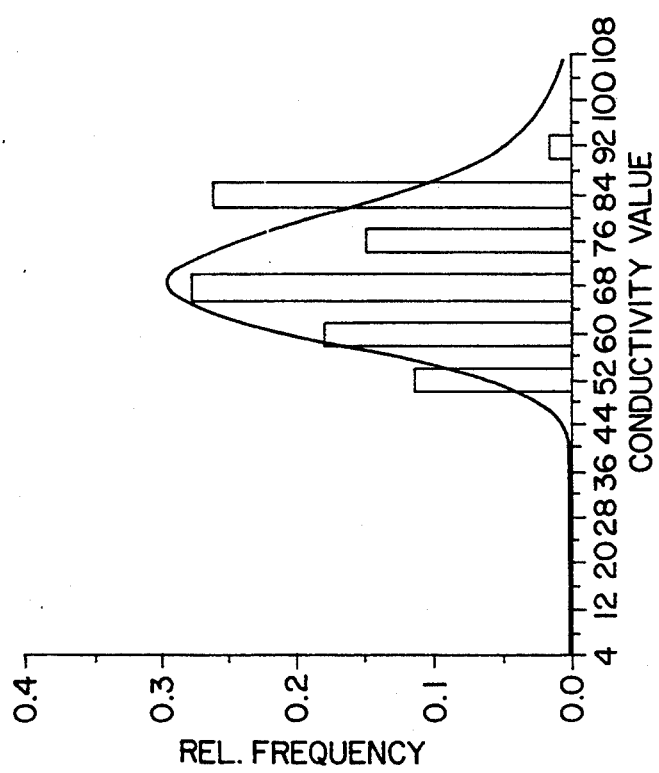

The data itself indicates neither an objective criterion for the health condition of the patient prior to treatment nor the degree of improvement following treatment, whereas when testing the frequencies p ( n ) in obtaining specific values of conductivity n as to their agreements with the logarithmic normal distribution (represented in FIGS. 1a and 1b by the solid line curve) we then find:

1) Before treatment there are significant deviations from the normal distribution (FIG. 1a) as well as in the deviations of the moments of third and higher order (FIG. 2a) defined as $$\left(m^r = \sum_{i=1}^{N} p(n_i) \cdot (n_i - \bar{n})r\right)$$

This indicates that the patient is not healthy, the nature and seriousness of the affliction being recognizable in this projection as the nature and degree of deviation from the logarithmic normal distribution.

2) Following treatment both a significantly better agreement with the logarithmic normal distribution (fig. 2b) and also a lesser deviation of the higher order moments from the ideal moments of the normal distribution are recognizable, the curves being transformed so that the moments of the first and second order (averages and variances) of the ideal and measured distribution agree.

| Measurement range | treatment | |
| --- | --- | --- |
| | before frequencies | after frequencies |
| 0–48 | 0 | 0 |
| 48–56 | 14 | 15 |
| 56–64 | 22 | 34 |
| 64–72 | 34 | 34 |

-continued

| Measurement range | treatment before frequencies | after frequencies |
| --- | --- | --- |
| 72–80 | 18 | 30 |
| 80–88 | 32 | 8 |
| 88–96 | 2 | 1 |
| 96–112 | 0 | 0 |

Up until now the invention has been described on the basis of measuring the electrical conductivity of the skin as the physiological characteristic. When other characterics are made use of the means of the invention must be modified accordingly. For example, the intensity with which the skin radiates in the infrared or optical range can be utilized as the characteristic. In this case proximity sensor elements are used preferably in an arrangement and number corresponding to that of the needle-shaped sensor elements of the embodiment already described. Other means for sensing the physiological characteristics can take the form of grid, roller or brush-type electrodes. Although, in addition, the above describes in particular the preferred assessment of the overall health condition of a test person on the basis of comparing the real distribution function to the ideal, i.e. logarithmic normal distribution of the measured values obtained from the test person, the invention is understood to also cover a comparison on the basis of a reference statistical distribution of the data established for the physiological characteristic in question from measurements made on a number of healthy individuals.

I claim:

1. A method of determining the health condition of a particular test individual on the basis of a comparison of a selected measured physiological characteristic of the test individual to a corresponding reference characteristic of a healthy condition comprising the steps of: detecting values of the selected physiological characteristic at a statistically significant plurality of measuring points distributed over a defined body region of the test individual, determining a statistical distribution of the detected values obtained for the body region of the test individual, determining a logarithmic reference normal distribution of the detected values, and comparing the statistical distribution of the detected values to the logarithmic reference normal distribution of the detected values Of the selected physiological characteristic.

2. A method according to claim 1, wherein a region of the skin of the test individual is employed as the body region.

3. A method according to claim 2, wherein the physiological characteristic to be measured is the conductivity of the skin to which a specific electric potential is applied.

4. A method according to claim 2, wherein the physiological characteristic to be measured is radiation intensity of skin.

5. A method according to claim 1, wherein deviations of the same order are determined from the comparison.

6. A method according to claim 1, wherein the statistical distribution is subjected to a correlation analysis.

7. A method according to claim 1, wherein deviations of frequencies of occurrences of the same orders of values are determined from the comparison.

8. An apparatus for determining the health condition of a particular test individual on the bases of a comparison of a selected measured physiological characteristic of the test individual to a corresponding reference characteristic of a healthy condition, said apparatus comprising:
    a sensor device comprising a plurality of sensing elements for detecting values of the selected physiological characteristic of the test individual at a plurality of measurement points distributed over a body region of the test individual;
    a processing means coupled to the sensor device for processing signals representative of the detected values of the physiological characteristics received from the sensor device;
    said processing means including a calculating processor means for calculating from the signals an actual statistical distribution of the detected values and for calculating a logarithmic normal distribution of the measured values.

9. An apparatus according to claim 8, wherein said sensor device includes a plurality of sensor elements distributed over a defined surface area of said body region and a means for successively scanning said sensor elements.

10. An apparatus according to claim 9, wherein said sensor elements include needle-shaped elements.

11. An apparatus according to claim 8, wherein said sensor device comprises sensor elements for obtaining the measured values by proximity.

12. An apparatus according to claim 8, wherein said sensor device includes electrodes arranged in a grid to detect the values of the physiological characteristic.

* * * * *